United States Patent
Kimura et al.

[19]

[11] Patent Number: 5,926,273
[45] Date of Patent: Jul. 20, 1999

[54] METHOD OF MEASURING THE ABSORPTION SPECTRA OF SOLUTIONS BY LASER INDUCED PHOTOTHERMAL DISPLACEMENT SPECTROSCOPY

[75] Inventors: Takaumi Kimura; Yoshiharu Kato; Zenko Yoshida, all of Ibaraki-ken, Japan

[73] Assignee: Japan Atomic Energy Research Institute, Tokyo, Japan

[21] Appl. No.: 08/864,693

[22] Filed: May 28, 1997

[30] Foreign Application Priority Data

May 31, 1996 [JP] Japan ................................ 8-137812

[51] Int. Cl.$^6$ .................................................. G01B 9/02
[52] U.S. Cl. ............................................ 356/349; 356/357
[58] Field of Search .................................. 356/349, 351, 356/357, 432, 432 T, 346, 345

[56] References Cited

U.S. PATENT DOCUMENTS

| | | | |
|---|---|---|---|
| 4,890,925 | 1/1990 | Kitamori et al. | 356/432 |
| 5,136,172 | 8/1992 | Nakata et al. | 356/432 |
| 5,404,224 | 4/1995 | Kotidis et al. | 356/351 |
| 5,479,259 | 12/1995 | Nakata et al. | 356/349 |

OTHER PUBLICATIONS

Stumpe, et al., Specification of Actinide Ions in Aqueous Solution by Laser-Induced Pulsed Photoacoustic Spectroscopy, Appl. Phys. B 34, 203–206 (1984).

Rojas, et al., Dual-Beam Optical Fiber Thermal Lens Spectroscopy, Analytical Chemistry, Sep. 15, 1991, pp. 1927–1932.

Bohnert et al., Use of Photothermal Deflection Spectrometry for Studies of Analytes in Aqueous Solutions, Fresenious J. Anal. Chem. (1990) 338:695–698.

*Primary Examiner*—Samuel A. Turner
*Attorney, Agent, or Firm*—Banner & Witcoff, Ltd.

[57] ABSTRACT

Improved method of laser induced photothermal displacement spectroscopy comprises the steps of applying pulsed laser light to the solution in a sample container, whereupon the light energy absorbed by the solution is converted to heat, with the resulting elastic wave displacing the wall of the sample container by vibrations, detecting the displacement by heterodyne interferometry, and measuring the absorption spectrum of the solution.

1 Claim, 4 Drawing Sheets

METHOD OF MEASURING THE ABSORPTION SPECTRA OF SOLUTIONS BY LASER INDUCED PHOTOTHERMAL DISPLACEMENT SPECTROSCOPY

BACKGROUND OF THE INVENTION

This invention relates to an improved method of laser induced photothermal displacement spectroscopy (LIPDS) which is suitable for measuring the absorption spectra of solutions such as those of highly radioactive samples by remote control in a non-contact manner.

According to the invention, the chemical state and concentration of a specific ion can theoretically be measured in a selective manner and, in addition, the measurement is real-time, continuous and automatic. Therefore, the method of the invention has a particular advantage in that uranium, transuranic elements, nuclear fission products, corrosion products, etc. in solutions that occur in the reprocessing of spent fuels from nuclear power generators, as well as in highly radioactive liquid wastes can be analyzed either qualitatively or quantitatively by an in-line process (remote controlled and in a non-contact manner) in accordance with the specific chemical state of ion. Stated more specifically, not only the oxidation state of radioactive ions but also various complexes thereof can be analyzed by selective measurements of the chemical states and concentrations of ions.

Absorptiometric analysis is a conventionally employed method for measuring the absorption spectrum of solutions. According to this method, the absorption of light that has passed through a sample is measured and the absorption wavelength of the sample provides for its qualitative analysis whereas the absorbance its quantitative analysis. The method has various salient features such as the ability to perform selective measurement and analysis of ion's chemical state and concentration, a capability for nondestructive analysis, rapidity in measurement and ease of operations in measurement.

While the chemical state and concentration of a particular ion can be selectively measured by several methods of analysis, absorptiometric analysis is the only method that can be applied in-line. Therefore, with a view to analyzing uranium and plutonium for achieving the accountability of nuclear fuels and the process control of facilities in the reprocessing of spent fuels from nuclear power generators, as well as for the purpose of monitoring the state of neptunium and other transuranic elements and for controlling their behavior, the development of a technology for in-line analysis by the absorptiometric approach is underway and there is an actual case of application of this method in the analysis of uranium.

Photothermal spectroscopy is known to be capable of measuring the chemical states and concentrations of ions in solution with higher sensitivity than absorptiometric analysis and examples of this technique include photoacoustic spectroscopy, thermal lens spectroscopy and photothermal deflection spectroscopy. In absorptiometric analysis, the intensity of light transmission through a sample solution is taken as relative to the light transmittance through a reference solution, so the sensitivity of this method is not dependent on the intensity of the light source. In contrast, photothermal conversion analysis measures the absorbed light energy, so the signal intensity obtained in this method is dependent on the intensity of the light source. Therefore, in photothermal conversion analysis, a high-intensity light source such as laser light is used as an exciting light source to thereby provide a higher sensitivity in measurement than absorptiometric analysis.

Photothermal conversion analysis is performed on two different principles; in one case, the light energy absorbed by a sample solution is converted to heat by non-radiation transition and the resulting elastic wave is detected with a piezoelectric device (as in photoacoustic spectroscopy); in the other case, a refractive index profile due to the thermal distribution produced by photothermal conversion is detected by optical means (as in thermal lens spectroscopy and photothermal deflection spectroscopy). However, either approach still remains a subject of basic research and no practical case has yet materialized in the actual process.

If absorptiometric analysis is to be applied to in-line analysis, fiber optics has to be used not only for introducing excitation light but also to detect transmitted light and this makes it necessary to consider the radiation resistance of fiber optics in a high radiation field. In photoacoustic spectroscopy which involves detection with a piezoelectric device, the introduction of excitation can be remotely controlled by using a laser but, on the other hand, the sample or sample container must be brought into direct contact with the piezoelectric device. Thermal lens spectroscopy and photothermal deflection spectroscopy have a possibility for realizing non-contact measurements by remote control but this approach is still at the stage of basic research.

SUMMARY OF THE INVENTION

An object, therefore, of the invention is to provide an improved method of laser induced photothermal displacement spectroscopy, in which a high-intensity, wavelength-tunable laser is used as an exciting light source and a heterodyne interferometer capable of highly precise measurement of light interference is used as a detector such that exciting laser light and detecting laser light are guided through air to thereby ensure that the absorption spectrum of a sample solution is measured by remote control in a completely non-contact manner.

The invention relates to an improved method of laser induced photothermal displacement spectroscopy that has solved the aforementioned problems of the conventional methods of absorptiometric analysis and photoacoustic analysis in association with the analysis of light absorption spectra. The solution is provided by using a heterodyne interferometer as detection means rather than the piezoelectric device used as a contact detector in the conventional method of photoacoustic spectroscopy.

Heterodyne interferometry is a technique in which a specified frequency shift is provided between two light beams that create interference fringes such that the intensity of the interference fringes which have been fixed on a time basis is converted to an electrical signal representing the shift frequency, with the phase of the signal being used to determine the phase of the initial interference fringes, namely, the phase of light. This method has the following salient features: it is entirely neutral to a vibrating body; being capable of converging light, the method is capable of localized measurements; it is immune to external vibrations; there is substantially no need for optical adjustments.

Stated briefly, the present invention provides a method of analyzing the chemical state and concentration of an ion in solution, which comprises the steps of:

applying pulsed laser light to the solution in a sample container, whereupon the light energy absorbed by the solution is converted to heat, with the resulting elastic wave displacing the wall of the sample container by vibrations;

detecting the displacement by heterodyne interferometry; and measuring the absorption spectrum of the solution.

In a specific embodiment of the invention, an exciting laser apparatus, a dye laser apparatus and a heterodyne interferometer are positioned remote from the sample container and the light from the dye laser apparatus as excited by the exciting laser light is introduced into the sample solution in the container through air and the optical energy of the excited light is absorbed by the sample solution so that it is converted to heat, and the vibrational displacement of the wall of the sample container due to the elastic wave generated in the process of heat generation is measured by the detecting light from and the reflected light to the heterodyne interferometer in a remote non-contact manner to provide the absorption spectrum of the sample solution, therey analyzing the chemical state and concentration of the specific ion in the sample solution.

DETAILED DESCRIPTION OF THE INVENTION

Figure 1:
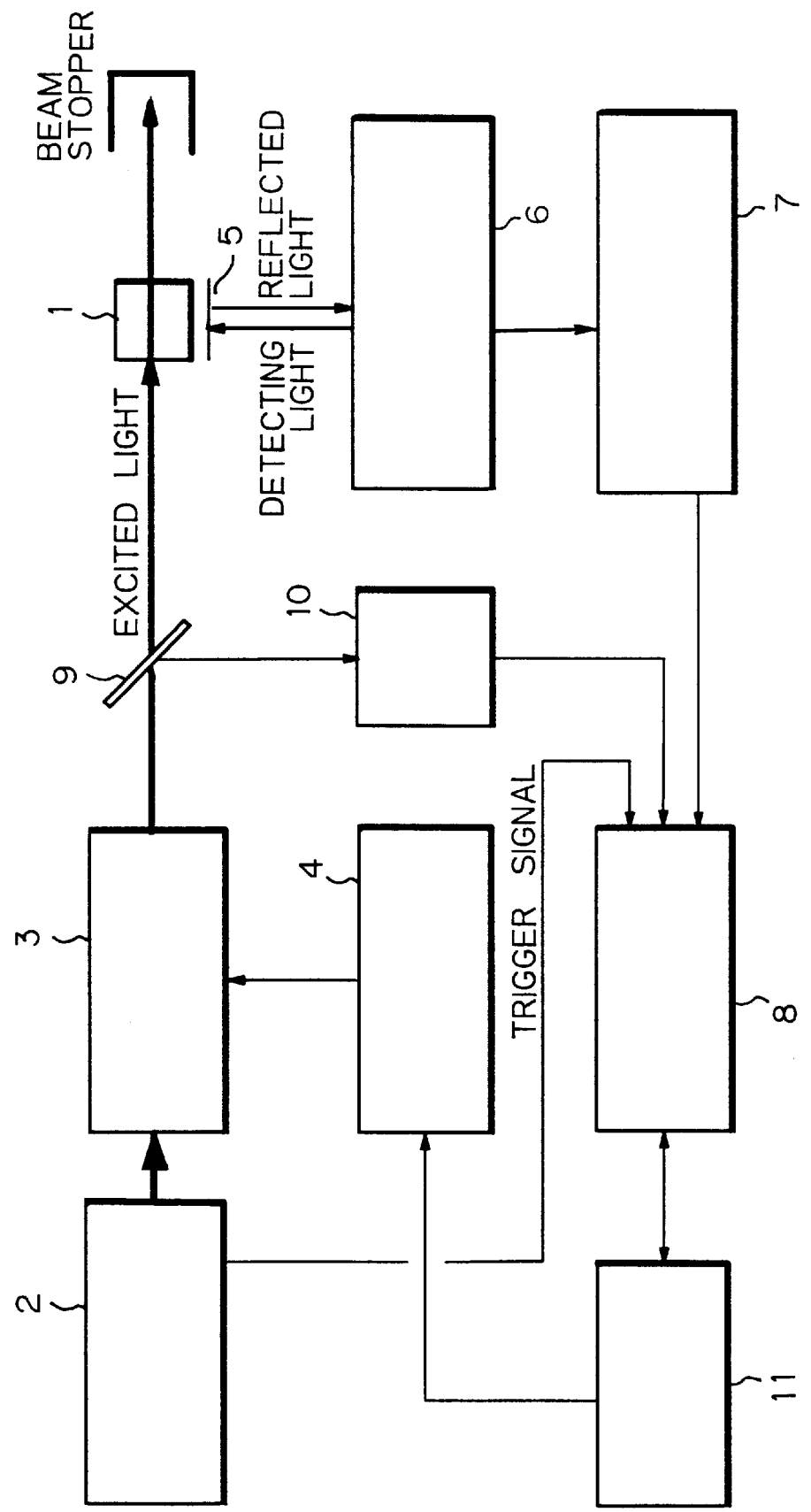
FIG. 1 is a diagram showing the layout of an apparatus for implementing the method of laser induced photothermal displacement spectroscopy of the invention.

The invention will now be described with reference to the accompanying drawings. An apparatus for use in the non-contact remote measurement of the absorption spectrum of a solution by laser induced photothermal displacement spectroscopy is shown in FIG. 1. A sample cell 1 is filled with a given volume of a sample solution to be analyzed. The sample solution is illuminated with light from a dye layer 3 excited with an Nd:YAG laser 2 (YAG designates the crystal of yttrium, aluminum and garnet which has been doped with neodymium to produce a lasing medium). The wavelength of the dye laser is set at a suitable value by a scan controller 4. The solute or solvent in the sample solution absorbs the energy of the excited light from the dye laser; the absorbed energy is converted to heat through the process of non-radiative transition and the resulting elastic wave causes the sample cell to vibrate.

The resulting small displacement of the wall of the cell is measured in a completely non-contact manner by the detecting light from and the reflected light to a heterodyne interferometer 6 which is focused at a reflector mirror 5 on a lateral side of the cell. The phase change in the light as detected with the heterodyne interferometer is converted to an electrical signal by means of a signal processor 7 and recorded on a digital storage oscilloscope 8. Subsequently, the recorded signal in the time domain is Fourier transformed to a signal in the frequency domain (FFT).

Since the power of the excited light from the dye laser is wavelength-dependent, the excited light is split with a beam splitter 9 provided ahead of the sample cell and the beamlet is monitored with a pyroelectric detector (PED) 10 and similarly recorded on the digital storage oscilloscope. If a maximum value of the FFT signal divided by the PED signal is plotted against the wavelength of the excited light, an absorption spectrum of a sample solution is obtained as shown by the single-peak curve in FIG. 2. The entire process of signal measurement and dye laser scanning outlined above is implemented in a completely automatic manner as instructed by a personal computer 11.

Figure 2:
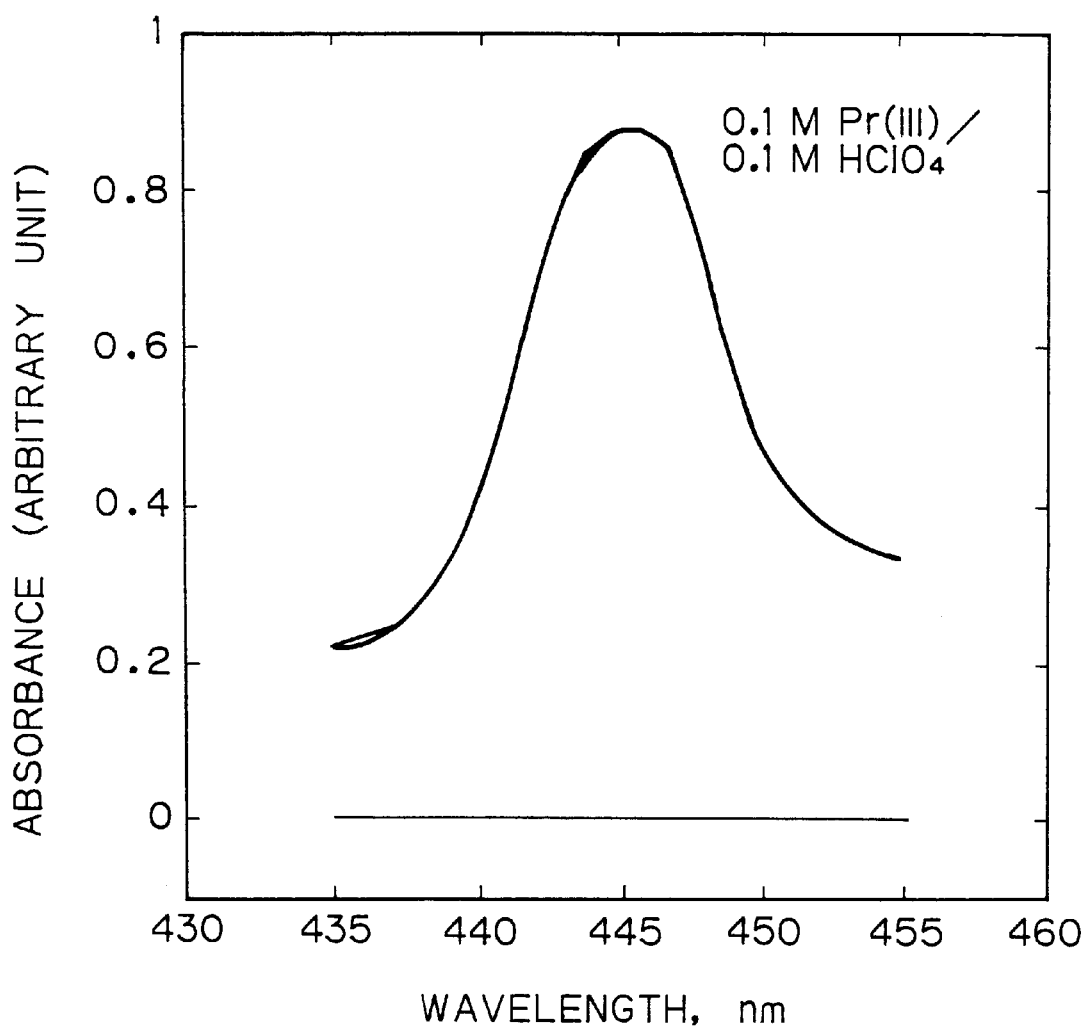
FIG. 2 is chart showing the absorption spectra of 0.1M Pr(III)/0.1M $HClO_4$ and 0.1M $HClO_4$ as obtained by measurement with the apparatus shown in FIG. 1.
Figure 3:
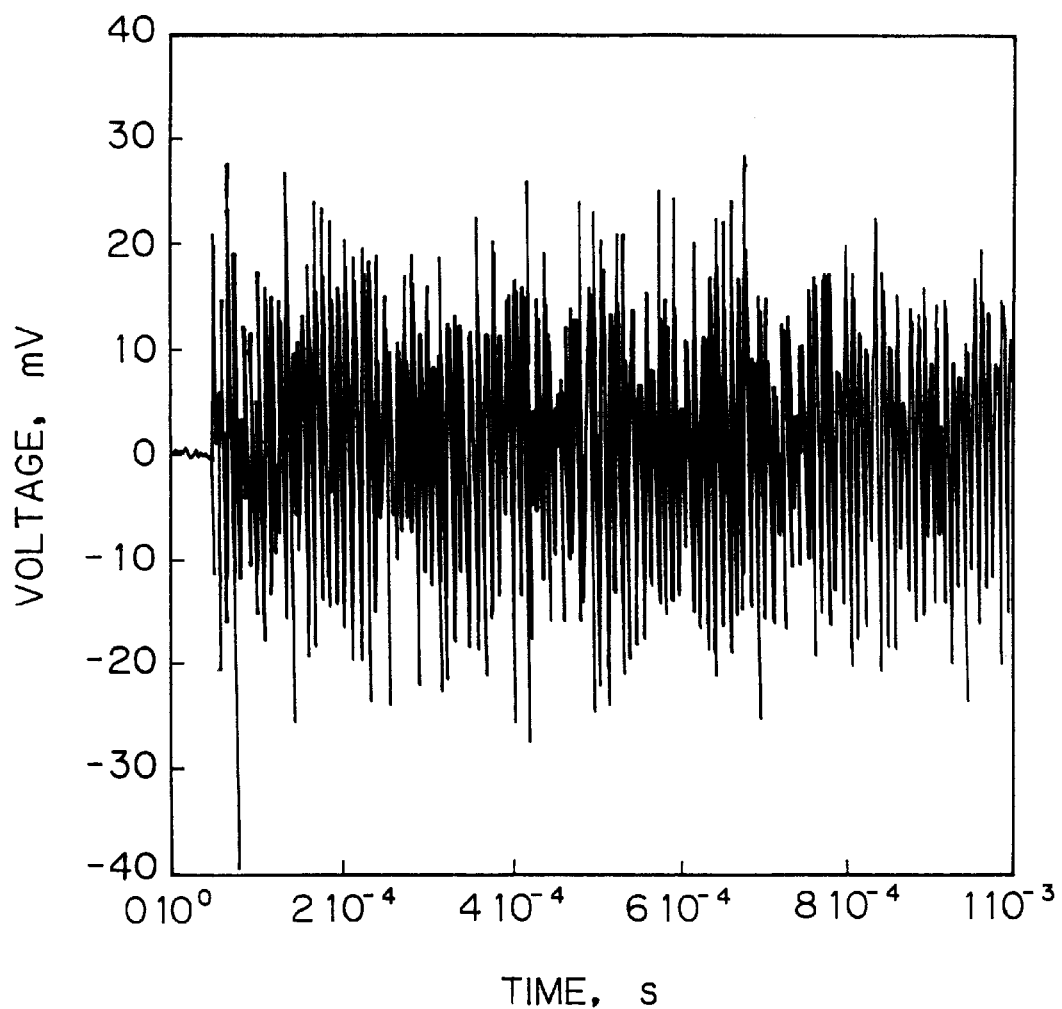
FIG. 3 is a chart showing the signal that was measured at a wavelength of 445 nm for the absorption of 0.1M Pr(III) with heterodyne interferometer 6 and signal processor 7 shown in FIG. 1 and which was recorded on digital storage oscilloscope 8.
Figure 4:
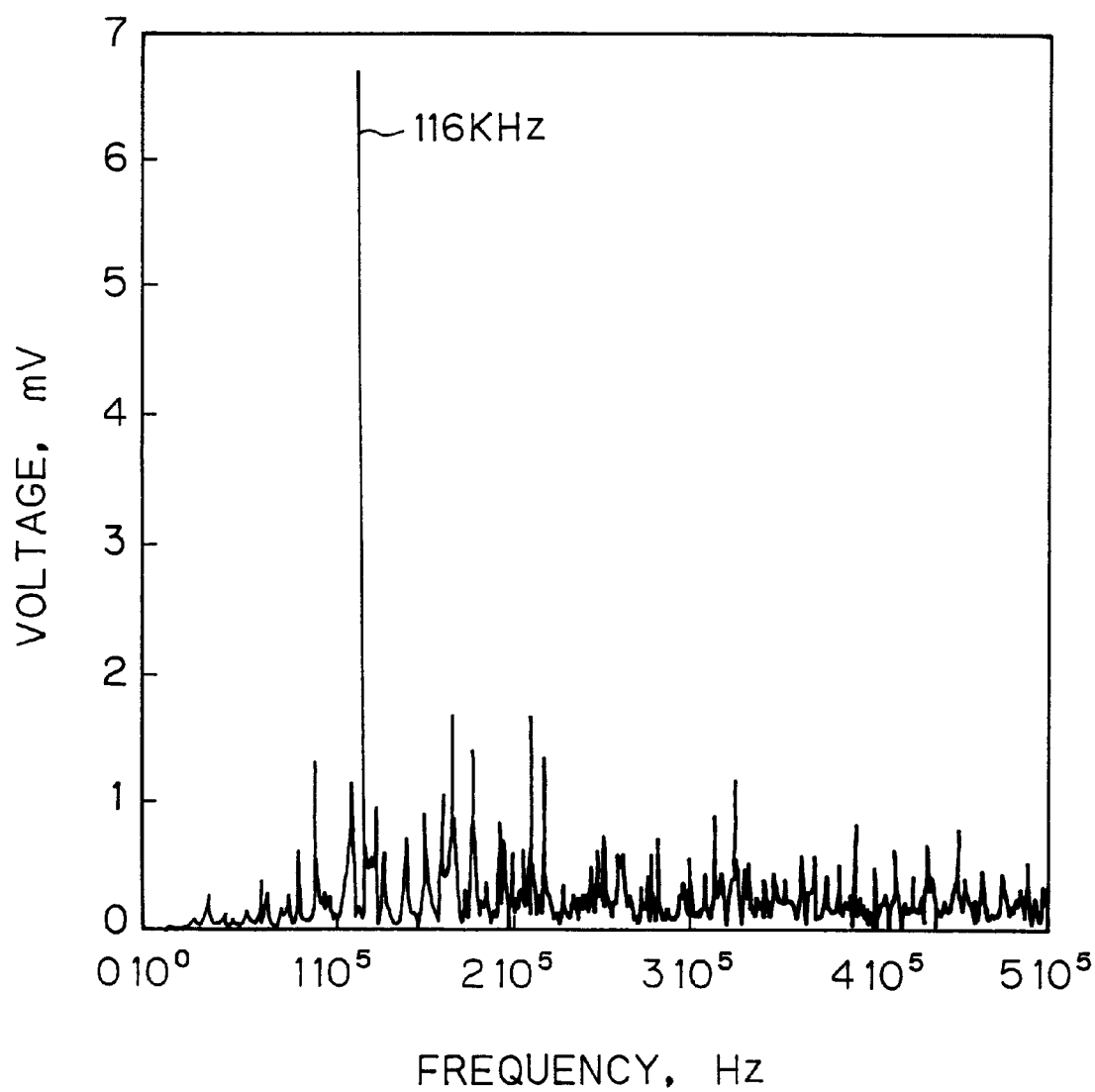
FIG. 4 is a scan of the Fourier transform of the electrical signal shown in FIG. 3.

The operating principle for the measurement of the absorption spectrum of a sample solution is described below more specifically with reference to the case where the sample solution consists of 0.1M Pr(III) in 0.1M $HClO_4$. As FIG. 2 shows, 0.1M Pr(III) has an absorption maximum at a wavelength of 445 nm and the signal measured at that wavelength by means of the heterodyne interferometer 6 and signal processor 7 shown in FIG. 3 and recorded on the digital storage oscilloscope is shown in FIG. 3. Pr(III) absorbs the light at 445 nm and the absorbed light energy is converted to heat and the resulting elastic wave (ultrasonic wave) vibrates the wall of the sample cell, as shown graphically in FIG. 3. The amplitude of the vibration represents the magnitude of the light energy absorbed by Pr(III). In order to visualize the magnitude of this energy, the electrical signal shown in FIG. 3 was Fourier transformed to give the result shown in FIG. 4. Obviously, the vibration shown in FIG. 3 is chiefly composed of a vibration at a frequency of 116 kHz, which corresponds to the frequency at which an ultrasonic wave experiences multiple reflections from the inner surface of the cell. Hence, a peak value of this frequency (FFT) is used in the measurement of absorption spectra.

Referring back to the dye laser, its output power with a certain dye is wavelength-dependent. This means that a correct absorption spectrum cannot be taken even if the obtained signal (FFT) is directly plotted against wavelength. Instead, the laser output power at varying wavelengths is monitored with the pyroelectric detector (PED) shown in FIG. 1 and the value of FFT/PED is plotted on the vertical axis of FIG. 2 to produce an absorption spectrum with respect to the excited light of a given output power.

If a sample solution provides an absorption spectrum of the curve shown in FIG. 2, it is identified as containing Pr (III) as a metallic ion (solute) since the spectrum has a peak at 445 nm. This is how qualitative analysis of Pr(III) is possible in accordance with the invention. If a calibration curve is preliminarily constructed for known concentrations of Pr(III) at the wavelength of 445 nm, the concentration of Pr(III) in an unknown sample can be determined (quantitative analysis).

The following example is provided for the purpose of further illustrating the present invention but is in no way to be taken as limiting.

EXAMPLE

Using a laser induced photothermal displacement spectroscopy of the layout shown in FIG. 1, the method of the invention was implemented to measure the absorption spectrum of a solution by remote control in a non-contact manner. A sample solution was prepared by dissolving 0.1M (=mol $dm^{-3}$) of praseodymium [Pr(III)] ions in 0.1M perchloric acid ($HClO_4$) and 1 ml of the sample solution was placed in a quartz cell (10×10 mm). The sample solution was illuminated with pulsed laser light at a wavelength of 435–455 nm in the absorption peak region of Pr(III) ion (molar absorption coefficient: 10.4 $M^{-1}$ $cm^{-1}$. The laser light oscillated at a repetition frequency of 10 Hz and produced pulses with a width of about 10 ns and a power of about 5 mJ per pulse. The absorption spectra of 0.1M Pr(III)/0.1M $HClO_4$ and 0.1M $HClO_4$ were measured twice and the results are shown in FIG. 2.

The vertical axis of FIG. 2 plots the absorbance normalized to a given laser output power. The absorption spectrum shown in FIG. 2 has a peak at the same wavelength as the spectrum of Pr(III) obtained by the conventional method of absorptiometric analysis. In addition, the reproducibility of the measurement is high. Since the absorbance of light by 0.1M $HClO_4$ is 0.0025±0.0003, it is anticipated that under the conditions described above, Pr(III) can be measured to a concentration as low as 0.0001M, which is about a tenth of the lower detection limit that can be achieved by the conventional method of absorptiometric analysis.

According to the method of the invention which uses a high-intensity wavelength-tunable laser as an excitation light source and a high-precision heterodyne interferometer as a detector, the absorption spectrum of a solution can be measrued by remote control in a completely non-contact manner. By measuring the absorption spectrum and absorbance of a sample solution, the solvent and solute in the solution can be analyzed both qualitatively and quantitatively. The sensitivity of detection by the method of the invention is higher than that achievable by the conventional method of absorptiometric analysis.

What is claimed is:

1. A method of identifying the type and concentration of a solute contained in a solution by laser induced photothermal displacement spectroscopy, the method comprising:

applying pulsed laser light to the solution in a sample container having a wall transparent to the pulsed laser light, whereupon light energy from the pulsed laser light absorbed by the solution is converted to heat, with the resulting elastic wave displacing and vibrating the wall;

detecting a phase change in the pulsed laser light due to the wall displacement with a heterodyne interferometer; converting the detected phase change to an electrical signal with a signal processor; and recording the electrical signal on a digital storage oscilloscope;

splitting one portion of the pulsed laser light with a beam splitter to monitor the power of the laser with a pyroelectric detector, and recording the monitored power on the digital storage oscilloscope;

thereby obtaining an absorption spectrum of the solution with respect to the wavelength of the pulsed laser light, wherein the spectrum has a single peak curve;

identifying a solute of the solution on the basis of the wavelength corresponding to the peak of the curve; and determining the concentration of the solute by comparing the absorption spectrum to a calibration curve of known concentrations of the solute;

wherein the exciting laser apparatus and the heterodyne interferometer are positioned remote from the sample container;

wherein the displacement of the wall is measured by detecting light from and reflected to the heterodyne interferometer which is focused on a reflecting mirror on a lateral side of the wall; and wherein the pulsed laser and the detecting light are guided through air to the solution and the mirror, thereby enabling measurement of the absorption spectrum in a non-contact manner.

* * * * *